(12) United States Patent
Veitch et al.

(10) Patent No.: US 7,091,864 B2
(45) Date of Patent: Aug. 15, 2006

(54) SAMPLE CONTAINER WITH RADIOFREQUENCY IDENTIFIER TAG

(75) Inventors: Jeffrey Douglas Veitch, Ware (GB); Robert Anthony Biddlecombe, Ware (GB)

(73) Assignee: Glaxo Group Limited, Greenford (GB)

( * ) Notice: Subject to any disclaimer, the term of this patent is extended or adjusted under 35 U.S.C. 154(b) by 470 days.

(21) Appl. No.: 10/297,079

(22) PCT Filed: May 2, 2001

(86) PCT No.: PCT/EP01/04880
§ 371 (c)(1),
(2), (4) Date: Nov. 27, 2002

(87) PCT Pub. No.: WO01/94016

PCT Pub. Date: Dec. 13, 2001

(65) Prior Publication Data

US 2004/0100415 A1    May 27, 2004

(30) Foreign Application Priority Data

Jun. 6, 2000   (GB)   ................................. 0013619.2

(51) Int. Cl.
*G08B 13/14* (2006.01)

(52) U.S. Cl. .................. 340/572.8; 235/375; 235/492; 340/10.51

(58) Field of Classification Search ............. 340/573.1, 340/572.1, 572.4, 540, 505, 539.1, 10.1, 340/5.2, 10.51, 572.8; 235/375, 487, 492; 422/102, 104; 700/245, 266
See application file for complete search history.

(56) References Cited

U.S. PATENT DOCUMENTS

| | | | |
|---|---|---|---|
| 4,679,426 A | 7/1987 | Fuller et al. |
| 4,724,427 A | 2/1988 | Carroll et al. |
| 4,817,822 A | 4/1989 | Rand et al. |
| 4,940,966 A | 7/1990 | Pettigrew et al. |
| 5,025,246 A | 6/1991 | Schenkel et al. |
| 5,321,619 A | 6/1994 | Matsuda et al. |
| 5,347,274 A | 9/1994 | Hassett |
| 5,363,842 A | 11/1994 | Mishelevich et al. |

(Continued)

FOREIGN PATENT DOCUMENTS

DE        19621179        11/1997

(Continued)

OTHER PUBLICATIONS

Finkenheller, RFID Handbuch, Carl Hanser Vertag, Munich, pp. 1, 9-10, 14-17, 155-182, and 248-250, (Jan. 1998). Note: pp. 14-17, 157-164, and 248 have been translated into English.

(Continued)

*Primary Examiner*—Thomas Mullen

(74) *Attorney, Agent, or Firm*—James P. Riek

(57) ABSTRACT

There is provided a sample container comprising a retainer for retaining a sample; and a radiofrequency identifier comprising an antenna for transmitting or receiving radiofrequency energy; an integrated circuit chip connecting with said antenna; and a carrier for the radiofrequency identifier; wherein the radiofrequency identifier is on the carrier and the carrier connects to the retainer.

7 Claims, 4 Drawing Sheets

U.S. PATENT DOCUMENTS

| | | | |
|---|---|---|---|
| 5,368,948 A | 11/1994 | Davies et al. | |
| 5,381,137 A | 1/1995 | Ghaem et al. | |
| 5,448,110 A | 9/1995 | Tuttle et al. | |
| 5,469,363 A | 11/1995 | Saliga et al. | |
| 5,491,473 A | 2/1996 | Gilbert | |
| 5,505,195 A | 4/1996 | Sallis et al. | |
| 5,507,277 A | 4/1996 | Rubsamen et al. | |
| 5,508,203 A | 4/1996 | Fuller et al. | |
| 5,516,692 A | 5/1996 | Berndt et al. | |
| 5,520,166 A | 5/1996 | Ritson et al. | |
| 5,528,221 A | 6/1996 | Jeuch et al. | |
| 5,541,604 A | 7/1996 | Meier et al. | |
| 5,549,101 A | 8/1996 | Trofast et al. | |
| 5,560,353 A | 10/1996 | Willemot et al. | |
| 5,582,795 A | 12/1996 | Nishina et al. | |
| 5,583,819 A | 12/1996 | Roesner et al. | |
| 5,587,578 A | 12/1996 | Serra | |
| 5,608,739 A | 3/1997 | Snodgrass et al. | |
| 5,629,981 A | 5/1997 | Nerlikar | |
| 5,682,143 A | 10/1997 | Brady et al. | |
| 5,706,801 A | 1/1998 | Remes et al. | |
| 5,755,218 A | 5/1998 | Ritson et al. | |
| 5,770,455 A | 6/1998 | Cargill et al. | |
| 5,771,657 A | 6/1998 | Lasher et al. | |
| 5,774,875 A | 6/1998 | Medeiros et al. | |
| 5,777,303 A | 7/1998 | Berney | |
| 5,792,668 A | 8/1998 | Fuller et al. | |
| 5,796,602 A | 8/1998 | Sarpe et al. | |
| 5,799,651 A | 9/1998 | Garby et al. | |
| 5,809,997 A | 9/1998 | Wolf | |
| 5,813,397 A | 9/1998 | Goodman et al. | |
| 5,821,524 A | 10/1998 | Horlbeck et al. | |
| 5,831,859 A | 11/1998 | Medeiros et al. | |
| 5,844,802 A | 12/1998 | Lepper et al. | |
| 5,856,788 A * | 1/1999 | Walter et al. | 340/10.2 |
| 5,874,214 A | 2/1999 | Nova et al. | |
| 5,874,896 A | 2/1999 | Lowe et al. | |
| 5,892,441 A | 4/1999 | Woolley et al. | |
| 5,898,370 A | 4/1999 | Reymond | |
| 5,920,054 A | 7/1999 | Uber | |
| 5,955,950 A | 9/1999 | Gallagher, III et al. | |
| 5,959,531 A | 9/1999 | Gallagher, III et al. | |
| 5,961,923 A | 10/1999 | Nova et al. | |
| 5,961,925 A | 10/1999 | Ruediger et al. | |
| 5,963,136 A | 10/1999 | O'Brien | |
| 5,963,368 A * | 10/1999 | Domanik et al. | 359/396 |
| 5,972,156 A | 10/1999 | Brady et al. | |
| 5,981,166 A | 11/1999 | Mandecki et al. | |
| 5,986,562 A | 11/1999 | Nikolich et al. | |
| 6,002,344 A | 12/1999 | Bandy et al. | |
| 6,008,727 A | 12/1999 | Want et al. | |
| 6,017,496 A | 1/2000 | Nova et al. | |
| 6,018,299 A | 1/2000 | Eberhardt et al. | |
| 6,025,780 A | 2/2000 | Bowers et al. | |
| 6,032,666 A | 3/2000 | Davies et al. | |
| 6,040,773 A | 3/2000 | Vega et al. | |
| 6,040,774 A | 3/2000 | Schepps et al. | |
| 6,046,003 A | 4/2000 | Mandecki et al. | |
| 6,049,278 A | 4/2000 | Guthrie et al. | |
| 6,051,377 A | 4/2000 | Mandecki | |
| 6,078,845 A | 6/2000 | Friedman et al. | |
| 6,147,604 A | 11/2000 | Wiklof et al. | |
| 6,148,815 A | 11/2000 | Wolf | |
| 6,202,642 B1 | 3/2001 | McKinnon et al. | |
| 6,259,654 B1 | 7/2001 | de la Huerga | |
| 6,294,999 B1 | 9/2001 | Yarin et al. | |
| 6,343,690 B1 * | 2/2002 | Britton et al. | 198/867.06 |
| 6,366,824 B1 | 4/2002 | Nair et al. | |
| 6,594,611 B1 | 7/2003 | Beffa | |
| 6,729,327 B1 | 5/2004 | McFarland | |
| 6,729,330 B1 | 5/2004 | Scarrott | |
| 6,839,604 B1 | 1/2005 | Godfrey | |
| 2002/0023441 A1 | 2/2002 | Bara et al. | |
| 2002/0119580 A1 * | 8/2002 | Corless et al. | 436/518 |
| 2002/0198618 A1 | 12/2002 | Madden et al. | |
| 2003/0011476 A1 | 1/2003 | Godfrey et al. | |
| 2003/0064029 A1 | 4/2003 | Tarara et al. | |
| 2003/0079744 A1 | 5/2003 | Bonney et al. | |
| 2003/0183226 A1 | 10/2003 | Brand et al. | |
| 2004/0025871 A1 | 2/2004 | Davies | |

FOREIGN PATENT DOCUMENTS

| | | |
|---|---|---|
| DE | 29819987 | 2/1999 |
| DE | 29915334 | 1/2000 |
| EP | 0586083 | 3/1994 |
| EP | 645631 | 3/1995 |
| EP | 727752 | 8/1996 |
| EP | WO 96/131790 | 10/1996 |
| EP | 786357 | 7/1997 |
| EP | 831410 | 3/1998 |
| EP | 853288 | 7/1998 |
| EP | 859299 | 8/1998 |
| EP | 895087 | 2/1999 |
| EP | 947952 | 10/1999 |
| EP | 1001265 | 5/2000 |
| GB | 2076259 | 9/1981 |
| GB | 2249001 | 4/1992 |
| GB | 2262452 | 6/1993 |
| GB | 2297225 | 7/1996 |
| GB | 2308947 | 4/1997 |
| GB | 2308947 | 7/1997 |
| GB | 2312595 | 10/1997 |
| GB | 2314418 | 12/1997 |
| GB | 2328281 | 2/1999 |
| WO | WO 92/12402 | 7/1992 |
| WO | WO 92/17231 | 10/1992 |
| WO | WO 94/07225 | 3/1994 |
| WO | WO 95/22365 | 8/1995 |
| WO | WO 96/31790 | 10/1996 |
| WO | WO 97/04338 | 2/1997 |
| WO | WO 97/07443 | 2/1997 |
| WO | WO 97/10896 | 3/1997 |
| WO | WO 98/05088 | 2/1998 |
| WO | WO 98/15853 | 4/1998 |
| WO | WO 98/26312 | 6/1998 |
| WO | WO 98/35243 | 8/1998 |
| WO | WO 98/46548 | 10/1998 |
| WO | 908840 | 4/1999 |
| WO | WO 99/35091 | 7/1999 |
| WO | WO 99/35516 | 7/1999 |
| WO | WO 99/48044 | 9/1999 |
| WO | WO 99/49408 | 9/1999 |
| WO | WO 99/50690 | 10/1999 |
| WO | WO 99/65002 | 12/1999 |
| WO | WO 99/65548 | 12/1999 |
| WO | WO 99/67099 | 12/1999 |
| WO | WO 00/03313 | 1/2000 |
| WO | WO 00/21030 | 4/2000 |
| WO | WO 00/21031 | 4/2000 |
| WO | WO 00/21032 | 4/2000 |
| WO | WO 99/21030 | 4/2000 |
| WO | WO 0025720 | 5/2000 |
| WO | WO 01/24690 | 4/2001 |
| WO | WO 01/63368 | 8/2001 |

OTHER PUBLICATIONS

Ultrakust Laborsystem, BARTEC Logistic Management, Schulstrasse 30, D-94239 Gotteszell, 1 page (1998).
Ultrakust, BARTEC Logistic Management, Schulstrasse 30, D-94239 Gotteszell, 2 pages (1998).

Grunert, Ultrakust BARTAG, BARTEC Logistic Management, Schulstrasse 30, D-94239 Gotteszell, 1 page (1999).

Ultrakust, BARTEC Logistic Management, Schulstrasse 30, D-94239 Gotteszell, 1 page (1998).

Grunert, Ultrakust BARTAG, BARTEC Logistic Management, Schulstrasse 30, D-94239 Gotteszell, 6 pages (2000).

* cited by examiner

SAMPLE CONTAINER WITH RADIOFREQUENCY IDENTIFIER TAG

This application is filed pursuant to 35 U.S.C. 371 as a United States National Phase Application of International Patent Application Serial No. PCT/EP01/04880 filed on 2 May 2001, which claims priority from GB 0013619.2 filed on 6 Jun. 2000 in the United Kingdom.

TECHNICAL FIELD

The present invention relates to a radiofrequency identifier (RFID) tag which is attached to a sample container as an identification aid. In particular the invention relates to the application of RFID tags to identify sample containers used in pharmaceutical clinical trials.

BACKGROUND TO THE INVENTION

There is a continued need within research and development organisations, particularly in the chemical and biological fields, to be able to identify individual samples undergoing preparation or analysis. In the pharmaceutical industry, these samples generally take the form of clinical, biological or chemical samples. The growing trend towards automation of sample preparation and assay within the pharmaceutical industry to satisfy new drug discovery, evaluation and clinical trial programmes, greatly increase the needs to identify unique samples accurately and rapidly.

Clinical trial studies, such as metabolism and toxicity studies, are used to aid development of potential drug candidates. These studies must comply with Good Laboratory Practice (GLP) and other regulatory requirements to satisfy national authorities where registration of the new drug is sought. In many cases, additional compliance requirements, such as Good Manufacturing Practice (GMP), must also be satisfied.

The processing, storing and handling of sample data, particularly of clinical trials samples, requires careful control to ensure data quality and security. It is now common practice within the pharmaceutical industry to attach textual and/or bar coded labels to clinical trial samples to identify them via a unique bar coded identifier. Whilst the use of bar codes has greatly improved the speed and accuracy of sample identification compared to sample identification based solely on visual text recognition, such processes are still time consuming and prone to errors. Considerable time is required to scan, and often re-scan, individual bar coded samples into databases, prior to any sample preparation or assay. The 'line of sight' also imposes restrictions on the speed and accuracy of reading. These restrictions on readability often lead to samples being manually entered into databases, thereby introducing more errors and time delays into the process.

The Applicants have now devised a method for identifying and recording samples which address the aforementioned problems associated with conventional, bar coded techniques. The method involves the attachment of a RFID tag to a sample container, the RFID tag having a memory structure which allows for large amounts of information to be stored thereon. The memory structure can be arranged such that parts of the memory are read-only, other parts are read/write and further parts are encrypted and password protectable. Transfer of information to or from the memory is readily achievable by the use of a reader that is typically remote from the sample container. The use of such readers thus eliminates the 'line of sight' requirement described above for barcodes and minimises the need for any manual handling. In further aspects, the reader can be arranged to simultaneously read and write to the memory of multiple RFID tags on multiple sample containers. The invention may be used alone or in combination with existing identification systems, such as barcode and textual identifiers.

A principal advantage of the present invention is the ability to store many types of information in different parts of the memory structure of the RFID tag. The information could, for example, include clinical trial compliance information written to the memory at various time points in the trial process, thereby providing a detailed and readily accessible sample history of the clinical trial sample. The information could also include a unique serial number stored in encrypted form or in a password protectable part of the memory that uniquely identifies the sample container.

U.S. Pat. No. 5,963,136 describes an interactive prescription compliance and life safety system which provides remote and on site verification of procedures related to the health status of a patient, including the taking of medicines. One element of this system is the use of a RFID tag attached to a vial containing a drug prescribed by a medical practitioner.

U.S. Pat. No. 5,771,657 describes an automatic prescription dispensing and packaging system whereby empty prescription bottles are labelled and loaded in assigned locations in a carrier. The carriers are identified by use of a RFID tag and associated reader.

SUMMARY OF INVENTION

According to one aspect of the present invention there is provided a sample container comprising a retainer for retaining a sample; and a radiofrequency identifier comprising an antenna for transmitting or receiving radiofrequency energy; an integrated circuit chip connecting with the antenna; and a carrier for the radiofrequency identifier; wherein the radiofrequency identifier is on the carrier and the carrier connects to the retainer.

The radiofrequency identifier can be any known radiofrequency identifier. Such identifiers are sometimes known as radiofrequency transponders or radiofrequency identification tags. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

In one aspect, the retainer is selected from the group consisting of tube, vial, well and microscope slide.

In another aspect, the retainer is sealable with a cap. The cap may, for example, be a screw lid cap or a snap-fit cap.

In a further aspect, the retainer comprises material selected from the group consisting of glass, organic polymer and metal.

In one aspect, the antenna is capable of transmitting or receiving radiofrequency energy having a frequency of 50 KHz to 2.5 GHz. The ultra high frequency (UHF) spectrum falls within this range. Preferably the antenna is adapted to transmit or receive radiofrequency energy having a frequency of 125 KHz. More preferably, the antenna is adapted to transmit or receive radiofrequency energy having a frequency of 13.56 MHz. Most preferably, the antenna is adapted to transmit or receive radiofrequency energy having a frequency of 2.4 GHz.

In another aspect, the radiofrequency identifier is adhesively mountable on the sample container. The carrier may, for example, be mounted on the sample container by use of an appropriate adhesive. The adhesive should be resistant to the temperature and pressure extremes (such as freezing, boiling, autoclaving) which the sample containers may be exposed to. Similarly, the RFID tag must be capable of functioning following exposure to high/low temperatures and pressures; typically the tags will operate following sterilisation in an oven (220° Celsius) or an autoclave (135° Celsius at 3 bar with direct exposure to saturated steam) and/or freezing at −200° Celsius during cold storage and/or sample preparation in liquid nitrogen. Preferably, the carrier is a rigid disc. More preferably, the carrier is a flexible label. Most preferably the carrier is a ring. Optionally, the carrier is mouldable to the retainer or the cap.

In a further aspect, the carrier bears a barcode thereon. The use of a barcode offers an additional means of identification. The RFID tags herein described may be used in combination and/or integrated with other traditional product labelling methods including visual text, machine-readable text and dot codes.

In yet another aspect, the carrier encases the radiofrequency identifier. Preferably, the carrier forms a hermetic seal for the radiofrequency identifier. More preferably, the carrier comprises an insulating material. Most preferably, the insulating material comprises a glass material.

In one aspect, the integrated circuit chip has a read only memory area.

In another aspect, the integrated circuit chip has a write only memory area.

In a further aspect, the integrated circuit chip has a read/write memory area.

Preferably, the integrated circuit chip has a one-time programmable memory area. More preferably, the one-time programmable memory area has a unique serial number. Most preferably, the integrated circuit chip has a pre-set, non-read or writeable memory area.

In one aspect, the integrated circuit chip has plural memory areas thereon. Preferably, any memory area contains data in encrypted form. More preferably, any memory area is password protected.

In a further aspect, the integrated circuit chip has plural memory areas thereon including a read only memory area containing a unique serial number, a read/write memory area which can be made read only; and a password protected memory area containing data in encrypted form.

In another aspect, the sample container retains a biological sample.

Preferably, the biological sample is for use in studies selected from the group consisting of clinical trials, pharmacokinetic studies, metabolism studies, toxicity studies and environmental fate studies.

More preferably, the biological sample is derived from material selected from the group consisting of water, soil, prion, virus, fungus, alga, bacterium, insect, nematode, fish, reptile, plant, bird, mammal and human.

More preferably, the biological sample is selected from the group consisting of blood, plasma, urine, cerebral spinal fluid, faeces, cell and tissue. Most preferably, the biological sample is selected from the group consisting of protein, peptide, amino acid, antibody, carbohydrate, oligosaccharide, lipid, glycolipid, glyceride, polynucleotide, oligonucleotide and nucleotide.

In a further aspect, the sample container retains a chemical sample.

Preferably, the chemical sample is for use in an analytical assay or synthesis reaction.

Preferably, the chemical sample is a drug candidate.

Optionally, the chemical sample is an agrochemical. Preferably, the agrochemical is selected from the group consisting of herbicide, insecticide, fungicide, rodenticide, nematocide, acaracide and plant growth regulator.

Optionally, the chemical sample is a marking material. Preferably, the marking material is selected from the group consisting of toner, ink, dye, pigment, acid and alkali.

Optionally, the chemical sample is a light-sensitive material.

According to another aspect of the present invention, there is provided a system for identifying a sample container comprising a sample container according to the present invention; a carrier for supporting the sample container; and a reader for reading data from the radiofrequency identifier by transmitting radiofrequency energy thereto and receiving radiofrequency energy therefrom.

In one aspect, the system comprises a plurality of sample containers supported within a carrier wherein the reader is capable of reading each radiofrequency identifier separately by differentiating between individual radiofrequency identifiers within the same antenna field.

Preferably, the carrier is selected from the group consisting of rack, carousel, array, micro well plate, square well plate, collection plate and tube block.

In another aspect, the reader is capable of reading multiple radiofrequency identifiers simultaneously by differentiating between individual radiofrequency identifiers within the same antenna field.

In a further aspect, the system additionally comprises a writer for writing data to the radiofrequency identifier by transmitting radiofrequency energy thereto. Preferably the writer forms part of the reader, which is thus a 'reader/writer'. More preferably, the reader/writer is capable of writing to multiple radiofrequency identifiers simultaneously by differentiating between individual radiofrequency identifiers within the same antenna field. Advantages of such a capability are both speed and the reduction in transcription errors.

In one aspect, the reader is capable of reading and/or writing to one or more radiofrequency identifiers simultaneously at low temperature within the range of 4° Celsius to −200° Celsius. Preferably, the temperature is in the range of −15° Celsius to −25° Celsius. More preferably, the temperature is in the range of −75° Celsius to −85° Celsius. Reading of, and writing to, the radiofrequency tag can therefore be conducted in a cold environment, such as a freezer or cold room.

In another aspect, the reader is connectable to a sample preparation device and the data are producible from the device. Preferably, the device is selected from the group consisting of weighing scales, solid dispensing system and liquid dispensing system.

In a further aspect, the system additionally comprises transferring the data from the reader to an electronic data management system comprising a memory for storage of data; a microprocessor for performing operations on said data; and a signal output for outputting a signal relating to the data or the outcome of an operation on the data.

Preferably, the electronic data management system is separate to the reader. More preferably the data are transferable from the reader to the electronic data management system via a public access or private access network computer system. The information can therefore be transferred from the reader to the electronic data management system via the Internet or a secure Intranet. Preferably the data are in encrypted form.

Optionally, the electronic data management system forms part of the reader.

Preferably, the electronic data management system forms part of a robotics system. More preferably, the robotics system employs an antenna to locate the position of the sample container according to the present invention. In another aspect, the system additionally comprises a data input system for user input of data to the electronic data management system. Preferably, the data input system comprises a man-machine interface. More preferably, the system additionally comprises a display for display of data from the electronic data management system to the user.

It is envisaged that data can be continuously read from sample containers within a controlled environment, such as a cold room or freezer, to determine their identity. These data could, for example, be combined with ongoing assay results which are continuously monitored within the controlled environment, such as chemical stability data, to record the assay data with time. The data could then be transferred to the electronic data management system via the Internet or a secure intranet.

According to another aspect of the present invention, there is provided a kit of parts comprising a sample container according to the present invention and a reader capable of reading and/or writing to each radiofrequency identifier separately or simultaneously by differentiating between individual radiofrequency identifiers within the same antenna field.

In a further aspect of the present invention there is provided a reader to identify individual sample containers according to the present invention within the same antenna field by transmitting radiofrequency energy thereto and by receiving radiofrequency energy therefrom.

BRIEF DESCRIPTION OF DRAWINGS

Embodiments of systems according to the invention will now be described with reference to the accompanying drawings in which:

FIG. 1b is a schematic side perspective of the sample container of FIG. 1a.

DETAILED DESCRIPTION OF THE DRAWINGS

Figure 1A:
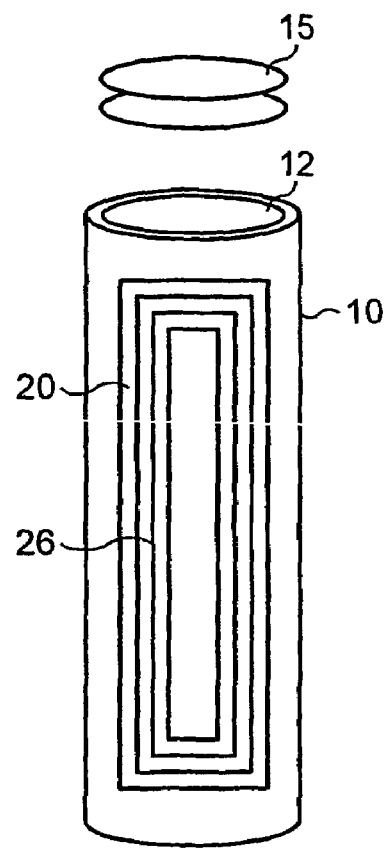
FIG. 1a is a schematic front perspective of a sample container according to the invention.

FIG. 1a is a front perspective showing a RFID tag 20 affixed to a sample container 10. Data can be received by, or transmitted from, the RFID chip (not shown) via antenna 26 which is connected to the chip. The antenna 26 is capable of receiving or transmitting radiofrequency energy over a wide bandwidth, ranging from 50 KHz to 2.5 GHz. A lid 15 may be pressed or screwed into position at the mouth 12 of container 10 to enclose the contents (not shown) of the container.

Figure 1B:
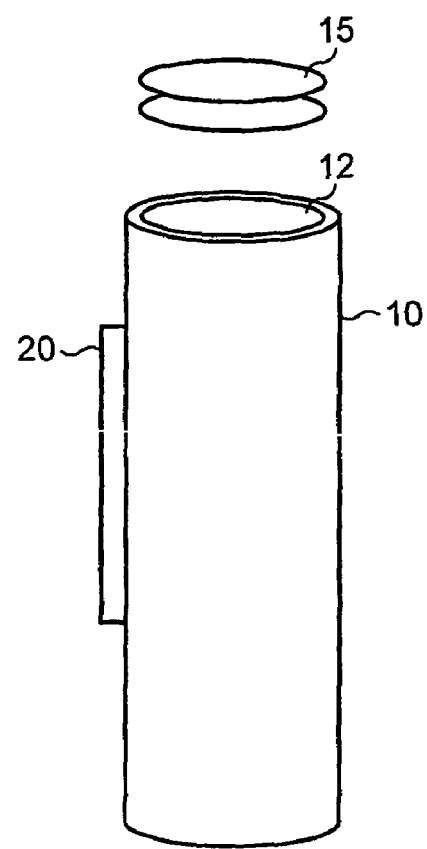

FIG. 1b shows a side perspective of the sample container of FIG. 1a. RFID tag 20 protrudes from the side of container 10 where it may be read or written to by a reader (not shown). To read data on the chip, the tag 20 is energised on receiving radiofrequency energy from the reader and returns information to the reader in radiofrequency waveform.

Figure 2:
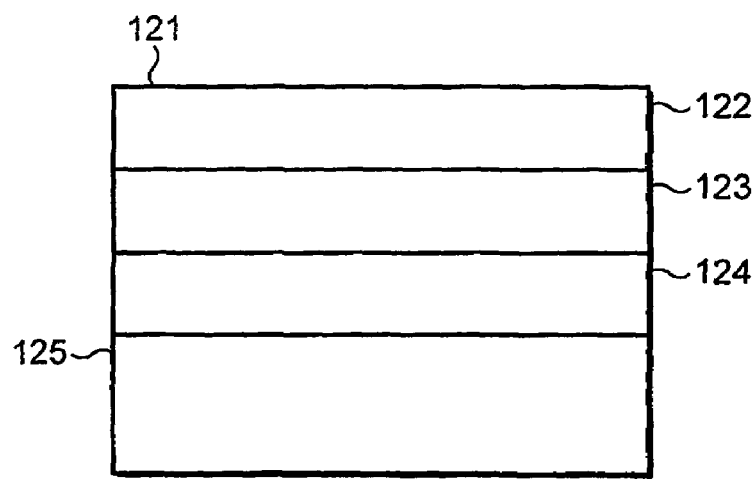
FIG. 2 is a simplified drawing of the memory of a RFID chip according to the invention.

FIG. 2 is a schematic representation of the memory structure of the RFID chip 121. Such tags are divided into unique blocks, typically numbering sixteen in total, with data being stored in non-volatile memory EEPROM, the EEPROM having a memory capacity of 512–2000 bits with each block consisting of 4 bytes. However, for the sake of simplicity, in the illustration shown in FIG. 2 the tag is divided into four blocks 122–125 only.

The first block 122 contains unique tag identifiers such as serial numbers and any details specified by the purchaser, this information being in a read-only format and being encoded on the tag at the time of manufacture such that this information cannot be altered once set.

The second block 123 permits write access conditions to be determined for the third and fourth blocks, 124 and 125, respectively, for example to allow read and write access to the remaining blocks. This block may be considered a 'secret area' in that access requires mutual authentication and enciphered data communications are used in this area. The second block 123 may be made read-only once information has been written to it; i.e. it may become one-time programmable.

The third block 124 enables special functionality to be written to the fourth block 125, for example to set encryption capabilities within this block 125.

The fourth block 125 can be considered to be a 'user' or 'public' area in that it may be programmed, by block two 123, such that information may be read from or written to it. This is generally the format in operation, information being read from and written to this area. Access can be password protected and data may be in encrypted format to enhance security.

In use, information from block one 122 (e.g. the unique serial number) will generally be used to identify the tag. Identification data (e.g. patient name, sex, age) will be transmitted from a writer (not shown) to block four 125, where it can stored and accessed by a reader (not shown). Additional sample information data, such as date stamps/original sample weight or volume, may also be written to this area. Thus specific samples can be identified from the RFID tag throughout the lifetime of the sample; for example, from initial sampling to final chemical analysis. Any data generated on a particular sample can be transferred to an electronic database (not shown) where they will be specifically identified against the unique identifier on the RFID tag. The electronic database may, for example, be a personal computer or form part of a Laboratory Information Management System (LIMS) and/or electronic inventory system.

Figure 3:
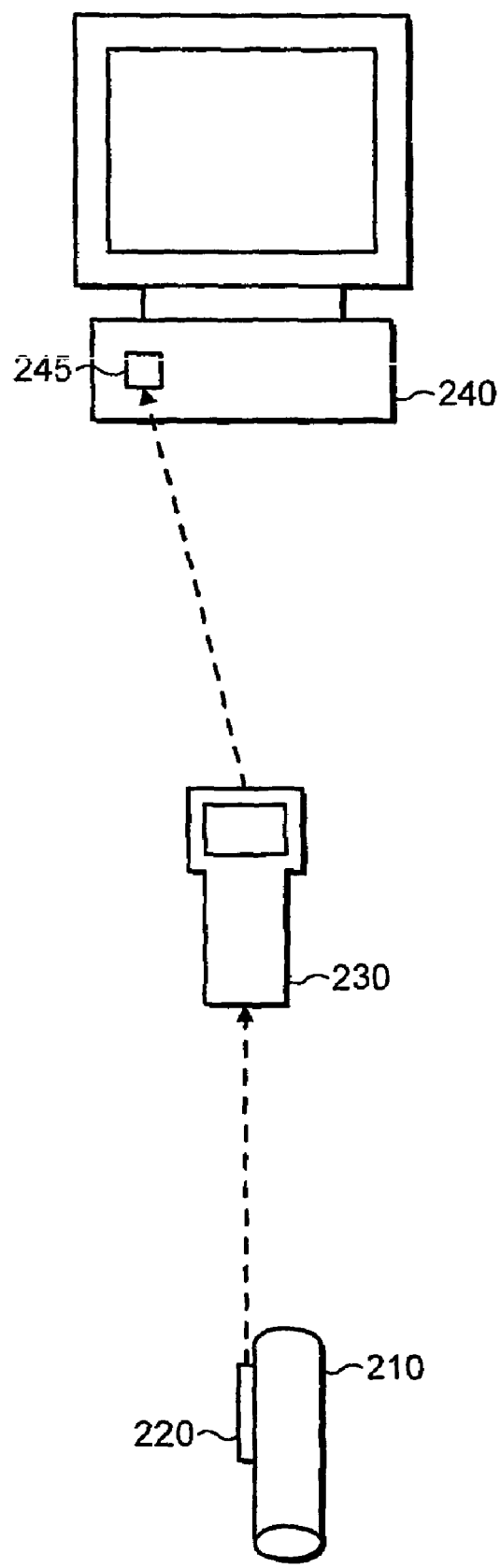
FIG. 3 is a schematic representation of a single sample container being identified according to the invention.

FIG. 3 is a diagram of a RFID tag 220 on an individual sample container 210 being read by reader 230. The reader may, for example, be a hand held device which transmits radiofrequency energy to the tag 220 and receives radiofrequency energy therefrom. The unique identifier and/or unique details in the data populated memory on tag 220 will identify the particular sample container 210. The information on the tag 220 may then be transferred from the reader 230 to sensor 245 on a local electronic database 240, such as a personal computer, by wireless means (e.g. infra red energy). Any new data which will be generated for the sample, as identified by the unique identifier, can then be added to the electronic database 240. The electronic database 240 may transfer the data to, or may form part of, a LIMS (not shown).

Figure 4:
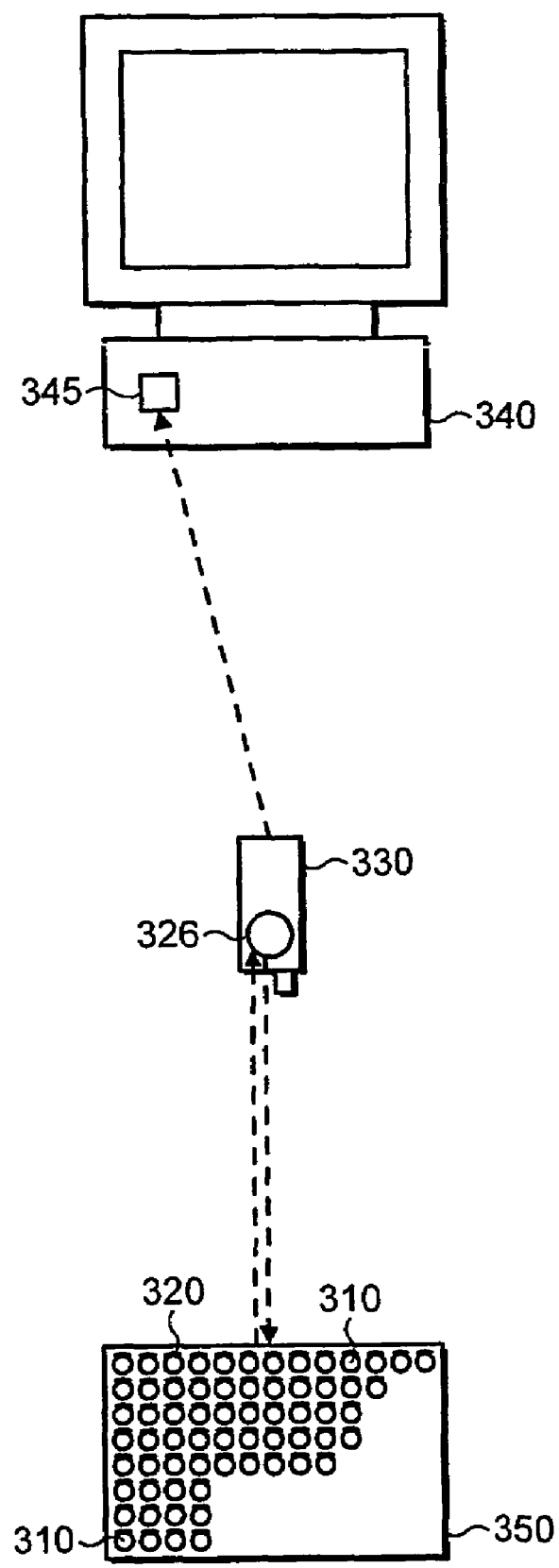
FIG. 4 is a schematic representation of a reader identifying individual sample containers within a carrier.

FIG. 4 shows a reader 330 reading sample container 310 held in a sample rack 350. The rack 350 holds a plurality of sample containers 310, each with a RFID tag 320. Each tag 320 has a unique identifier encoded on the memory chip (not shown). On receiving radiofrequency energy from the reader 330, tag 320 transmits information as radiofrequency energy to the antenna 326 on reader 330. This information uniquely identifies the sample container 310. The information may then be transmitted to sensor 345 attached to a local electronic database 340 by wireless means, such as infra red energy. Each sample container 310 will therefore be identified and any additional data, generated for example in a chemical analysis, may be added to the information for the specific sample on the database. The date and time of generation of the data will also be recorded. The database 340 may transfer the information to, or form part of, a LIMS (not shown), thereby providing a complete electronic history of the clinical trial sample.

Figure 5:
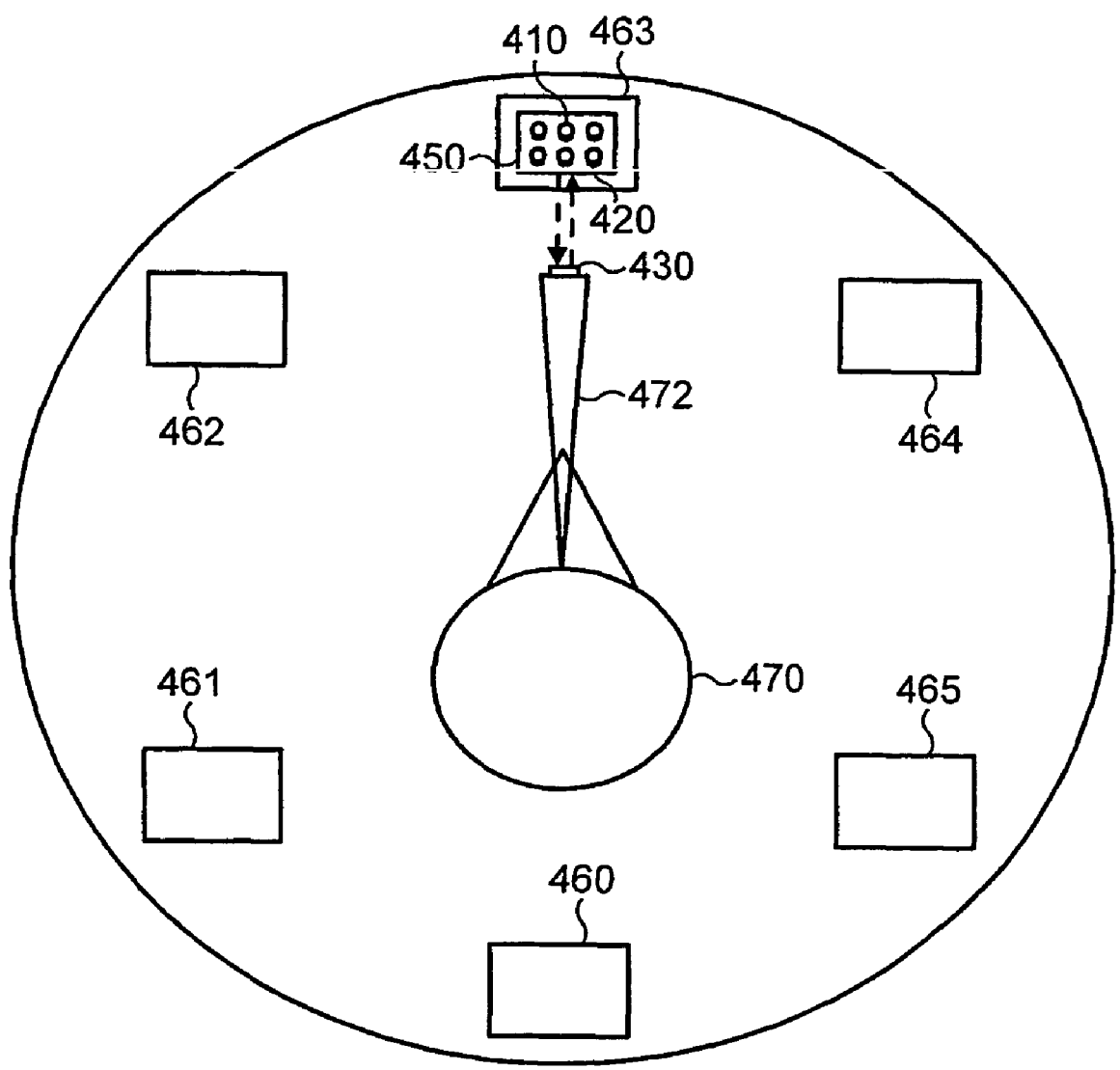
FIG. 5 is a schematic representation of a robotic arm system identifying sample containers at various workstations and/or peripheral devices.

FIG. 5 shows a robotic arm system 470 identifying sample contains 410 at workstations 460–465. The robotic arm system 470 may be used to carry out a series of operations on the samples within each sample container 410, such as a chemical reaction/assay. The RFID tags 420 are used to identify each sample container 410 throughout the procedure.

The robotic arm 472 is free to rotate 360 degrees around its axis, thereby accessing workstations and/or peripheral devices 460 to 465. RFID tags 420 are attached to sample containers 410 within rack 450. The robotic arm can move the rack 450 to each of the workstations and/or peripheral devices 460–465 in order that different operations are carried out on the samples within each sample container 410.

In the example shown in FIG. 5, involving a typical chemical analysis, a reader/writer 430 attached to the robotic arm 472 identifies each sample container 410 in rack 450 by energising the RFID tag 420 and receiving radiofrequency energy carrying the unique identification number. Having identified the sample container 410, a solvent is added to each container by a liquid dispenser at workstation 460. This information, such as the nature/volume of the liquid and date/time of addition, may be written (not shown) to the RFID tag 420 by the liquid dispenser. The rack 450 is then moved by the robotic arm 472 to the second workstation 461 where the samples in the sample containers 410 are dried. On moving rack 450 to the third work station 462, each sample container 410 is again identified by the reader 430 and a known volume of diluent added (again this information may be transmitted to the RFID tag 420 by the liquid dispenser—not shown). The rack 450 is moved to the fourth work station 463 and a liquid reagent added to each sample container 410 by a dispenser, following identification by reader 430 on the robotic arm. The dispenser may transmit information regarding the reagent to the RFID tag 420. Incubation of the sample containers 410 occurs on moving the rack 450 to a heated water bath at workstation five 464. The reaction is terminated by the addition of a liquid reagent to each sample container 410 at the sixth work station 465 following identification using the RFID tag as described above.

It may be appreciated that any of the parts of the invention herein described which contact the sample (such as a chemical, biological or medical sample) may be coated with materials such as fluoropolymer materials which reduce the tendency of the sample to adhere thereto. Suitable fluoropolymers include polytetrafluoroethylene (PTFE) and fluoroethylene propylene (FEP).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

The invention claimed is:

1. A system for identifying a sample container comprising:
   a) a sample container comprising:
      a retainer for retaining a sample; and
      a radiofrequency identifier comprising:
         an antenna for transmitting or receiving radiofrequency energy;
         an integrated circuit chip connecting with said antenna; and
      a carrier for said radiofrequency identifier;
         wherein the radiofrequency identifier is on said carrier and the carrier connects to said retainer;
   b) a carrier for supporting the sample container; and
   c) a reader for reading data from the radiofrequency identifier by transmitting radiofrequency energy thereto and receiving radiofrequency energy therefrom,
   wherein the reader is capable of reading from and/or writing to one or more radiofrequency identifiers simultaneously at low temperature within the range of 4° Celsius to −200° Celsius.

2. A system according to claim 1, wherein said temperature is in the range of −15° Celsius to −25° Celsius.

3. A system according to claim 1, wherein the temperature is in the range of −75° Celsius to −85° Celsius.

4. A system for identifying a sample container comprising:
   a) a sample container comprising:
      a retainer for retaining a sample; and
      a radiofrequency identifier comprising:
         an antenna for transmitting or receiving radiofrequency energy;
         an integrated circuit chip connecting with said antenna; and
      a carrier for said radiofrequency identifier;
         wherein the radiofrequency identifier is on said carrier and the carrier connects to said retainer;
   b) a carrier for supporting the sample container;
   c) a reader for reading data from the radiofrequency identifier by transmitting radiofrequency energy thereto and receiving radiofrequency energy therefrom: and
   d) a writer for writing data to the radiofrequency identifier by transmitting radiofrequency energy thereto, wherein said writer forms part of the reader, and
   wherein the reader is connectable to a sample preparation device and said data are producible from said device.

5. A system according to claim 4, wherein the device is selected from the group consisting of weighing scales, solid dispensing system and liquid dispensing system.

6. A system for identifying a sample container comprising:
   a) a sample container comprising:
      a retainer for retaining a sample; and
      a radiofrequency identifier comprising:

an antenna for transmitting or receiving radiofrequency energy;
an integrated circuit chip connecting with said antenna; and
a carrier for said radiofrequency identifier;
wherein the radiofrequency identifier is on said carrier and the carrier connects to said retainer;
b) a carrier for supporting the sample container;
c) a reader for reading data from the radiofrequency identifier by transmitting radiofrequency energy thereto and receiving radiofrequency energy therefrom, and
d) an electronic data management system comprising:
a memory for storage of data;
a microprocessor for performing operations on said data; and
a signal output for outputting a signal relating to the data or the outcome of an operation on the data,
wherein said data from the reader is transmitted to said electronic data management system, and
wherein the electronic data management system forms part of a robotics system.

7. A system according to claim 6, wherein said robotics system employs an antenna to locate the position of said sample container.

* * * * *